United States Patent
Greaves

(10) Patent No.: US 10,456,607 B2
(45) Date of Patent: Oct. 29, 2019

(54) PHOTOACTIVE GRAFTED POLYSACCHARIDE AND USE THEREOF IN COSMETICS

(71) Applicant: L'OREAL, Paris (FR)

(72) Inventor: Andrew Greaves, Magny-le-Hongre (FR)

(73) Assignee: L'OREAL, Paris (FR)

( * ) Notice: Subject to any disclaimer, the term of this patent is extended or adjusted under 35 U.S.C. 154(b) by 221 days.

(21) Appl. No.: 15/529,215

(22) PCT Filed: Nov. 30, 2015

(86) PCT No.: PCT/EP2015/078001
§ 371 (c)(1),
(2) Date: May 24, 2017

(87) PCT Pub. No.: WO2016/083614
PCT Pub. Date: Jun. 2, 2016

(65) Prior Publication Data
US 2017/0361131 A1    Dec. 21, 2017

(30) Foreign Application Priority Data
Nov. 28, 2014   (FR) .................................... 14 61656

(51) Int. Cl.
| | | |
|---|---|---|
| A61Q 19/08 | (2006.01) | |
| A61K 8/73 | (2006.01) | |
| C08B 37/00 | (2006.01) | |
| C08B 37/08 | (2006.01) | |

(52) U.S. Cl.
CPC ................ *A61Q 19/08* (2013.01); *A61K 8/73* (2013.01); *A61K 8/731* (2013.01); *A61K 8/735* (2013.01); *C08B 37/0069* (2013.01); *C08B 37/0072* (2013.01); *A61K 2800/54* (2013.01)

(58) Field of Classification Search
None
See application file for complete search history.

(56) References Cited

FOREIGN PATENT DOCUMENTS

FR    2991583 A1    12/2013

OTHER PUBLICATIONS

Laville et al., "Polysaccharide-covered nanoparticles with improved shell stability using click-chemistry strategies", Carbohydrate Polymers, 93 (2013) 537-546.
Anonymous, "Photoreactive Crosslinker Chemistry", Life Technologies, Jun. 24, 2015.
Such et al., "Synthesis and functionalization of nanoengineered materials using click chemistry", Progress in Polymer Science, 37 (2012) 985-1003.
Takahashi et al., "In Situ Cross-Linkable Hydrogel of Hyaluronan Produced via Copper-Free Click Chemistry", Biomacromolecules, 14 (2013) 3581-3588.

*Primary Examiner* — Robert A Wax
*Assistant Examiner* — Randeep Singh
(74) *Attorney, Agent, or Firm* — Polsinelli PC

(57) ABSTRACT

The invention relates to a polysaccharide polymer of formula (I):

$$PS—(O—CO-L-X)_a(OH)_b \quad (I)$$

in which PS denotes the basic backbone of the polysaccharide bearing the hydroxyl groups;
L is a divalent hydrocarbon-based group comprising from 1 to 20 carbon atoms;
X denotes a photoactive group of azide or diazirine type;
a denotes the content of OH groups substituted with the photoactive group;
b denotes the content of unsubstituted free OH groups;
a being between 0.02 and 0.5; b being between 0.5 and 0.98; and a+b=1.
The invention also relates to a composition comprising the polymer (I) in a physiologically acceptable medium, and also to a cosmetic process for caring for the skin, comprising the topical application to the skin of said composition and exposure of the treated skin to light radiation.

29 Claims, No Drawings

PHOTOACTIVE GRAFTED POLYSACCHARIDE AND USE THEREOF IN COSMETICS

CROSS REFERENCE TO RELATED APPLICATIONS

This application is a National Phase filing under 35 U.S.C. § 371 of PCT/EP2015/078001 filed on Nov. 30, 2015; and this application claims priority to Application No. 1461656 filed in France on Nov. 28, 2014 under 35 U.S.C. § 119. The entire contents of each application are hereby incorporated by reference.

The present invention relates to a process for attenuating wrinkles on the skin, using a composition comprising a polysaccharide polymer grafted with a particular photoactive group, and exposure of the treated skin to light.

During the aging process, various signs appear on the skin which are very characteristic of this aging, being reflected in particular by a modification of skin structure and functions. The main clinical signs of skin aging are in particular the appearance of deep wrinkles and fine lines, which increase with age.

It is known to treat these signs of aging using cosmetic or dermatological compositions containing active agents capable of combating aging, such as α-hydroxy acids, β-hydroxy acids and retinoids. These active agents act on wrinkles by eliminating dead skin cells and by accelerating the cell renewal process. However, these active agents have the drawback of being effective for the treatment of wrinkles only after a certain application time. In point of fact, it is increasingly sought to obtain an immediate effect of the active agents used, rapidly resulting in smoothing-out of wrinkles and fine lines and in the disappearance of the signs of fatigue.

The inventors have discovered that the topical application to the skin of a polysaccharide polymer grafted with photoactive groups of azide or diazirine type, combined with exposure of the treated skin to light radiation, forms a film that especially has an improved tensioning effect on the skin and thus makes it possible rapidly to attenuate wrinkles on the skin. The film obtained shows good resistance to water and to sweat. The tensioning effect of the film on the skin also shows good resistance to water and thus good persistence with respect to water, and also to sweat and sebum. The polymer deposit obtained after exposure to light is also resistant to the mechanical stresses of the skin (generated by the movements of the skin).

More specifically, a subject of the present invention is a process, especially a cosmetic process, for caring for the skin, more particularly facial skin, in particular wrinkled skin, comprising:

(i) a step consisting in applying to the skin a composition, especially a cosmetic composition, comprising, in a physiologically acceptable medium, a polysaccharide polymer grafted with photoactive groups of azide or diazirine type of formula (I) as defined below;

(ii) a step consisting in exposing the treated skin to light radiation, preferably for at least 5 seconds. This step can be repeated several times during the day.

The process according to the invention is in particular intended for smoothing out human facial and/or bodily skin and/or for reducing or eliminating the signs of skin aging, in particular for reducing or eliminating wrinkles and/or fine lines of the skin.

The term "tensioning agent" means compounds that are capable of having a noticeable tensioning effect, i.e. of smoothing out the skin and rapidly, or even immediately, reducing the wrinkles and fine lines, or even making them disappear.

The tensioning effect can be characterized by an in vitro retraction test as described in example 1.

The polysaccharide polymer grafted with photoactive groups of azide or diazirine type corresponds to formula (I) below:

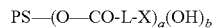

in which PS denotes the basic backbone of the polysaccharide bearing the hydroxyl groups;

L is a linear, branched or cyclic, saturated or unsaturated divalent hydrocarbon-based group comprising from 1 to 20 carbon atoms, preferably from 2 to 10 carbon atoms, which may be interrupted with one or more non-adjacent heteroatoms chosen from sulfur, oxygen, or —NH—, —COO—, —CO—NH—, —O—CO—NH— or —NH—CO—NH— groups, said divalent group being optionally substituted with one or more groups chosen from hydroxyl, amine, thiol, carboxylic acid, amide, cyano, and acyl $(C_1\text{-}C_4)$amino groups;

X denotes a photoactive group of azide or diazirine type;

a denotes the content of OH groups substituted with the group —CO-L-X;

b denotes the content of unsubstituted free OH groups;

a being between 0.02 and 0.5; b being between 0.5 and 0.98;

a+b=1

For example, when a=b=0.5, this means that half of the hydroxyl groups of the polysaccharide are grafted with the group —CO-L-X and the other half of the hydroxyl groups are not grafted, corresponding to the grafted polymer of formula

Preferably, a is between 0.02 and 0.4; b is between 0.6 and 0.98. Preferentially, a is between 0.02 and 0.3; b is between 0.7 and 0.98. More preferentially, a is between 0.04 and 0.2; b is between 0.8 and 0.96. Better still, a is between 0.04 and 0.15; b is between 0.85 and 0.96.

The polysaccharide may comprise, in addition to the hydroxyl groups, additional groups such as carboxylic acid, amino (—$NH_2$), aminoacetyl (—NHAc). These additional groups form part of the basic backbone of the polysaccharide bearing the hydroxyl groups.

The polysaccharide may comprise one or more base units chosen from uronic acid, glucuronic acid and mannuronic acid, preferably uronic acid.

The polysaccharide used according to the invention may be chosen from hyaluronic acid, chondroitin, chondroitin sulfate, alginic acid, heparin, heparin sulfate, xanthan gum, dextran and cellulose.

Preferably, the polysaccharide is hyaluronic acid or alginic acid. Preferentially, the polysaccharide is hyaluronic acid.

Hyaluronic acid is a linear glycosaminoglycan composed of repeating D-glucuronic acid and N-acetyl-D-glucosamine units linked together via alternating beta-1,4 and beta-1,3 glycosidic linkages.

Advantageously, the grafted polysaccharide has a weight-average molecular weight ranging from 5000 to 1 000 000 daltons, preferably ranging from 10 000 to 500 000 daltons, and even more preferentially ranging from 15 000 to 350 000 daltons.

The molecular weight may especially be determined by liquid chromatography, the eluent being 0.1 M sodium chloride and 330 mg/l of sodium azide in water, with dextran as standard, and Wyatt Optilab T-Rex refractometer and Wyatt Dawn-Heleos II light scattering detectors.

Preferably, the grafted polysaccharide is a grafted hyaluronic acid comprising grafted units having the following formula:

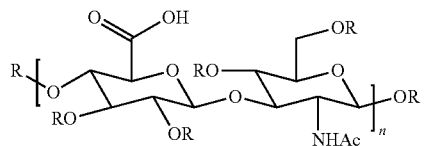

in which R independently represents H or a group —CO-L-X, L and X having the meanings described previously, it being understood that the grafted polysaccharide has a degree of grafting ranging from 2 to 50%.

n especially being such that the grafted polymer has a molecular weight as defined previously.

Preferably, the group L is chosen from the following groups:

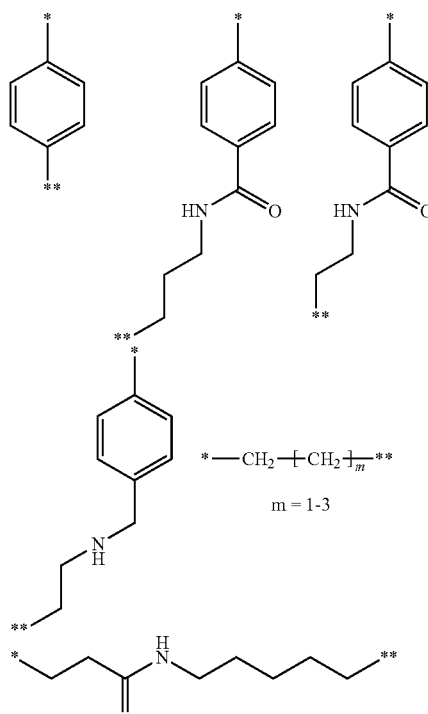

* representing the bond with the photoactive group X
** representing the bond with the ester group bonded to the polymer PS (PS—O—CO— group)

The photoactive group X may be chosen from the following groups:

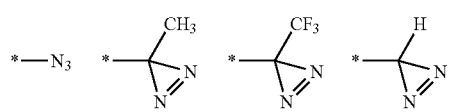

As examples of groups X-L-, mention may be made of the following groups:

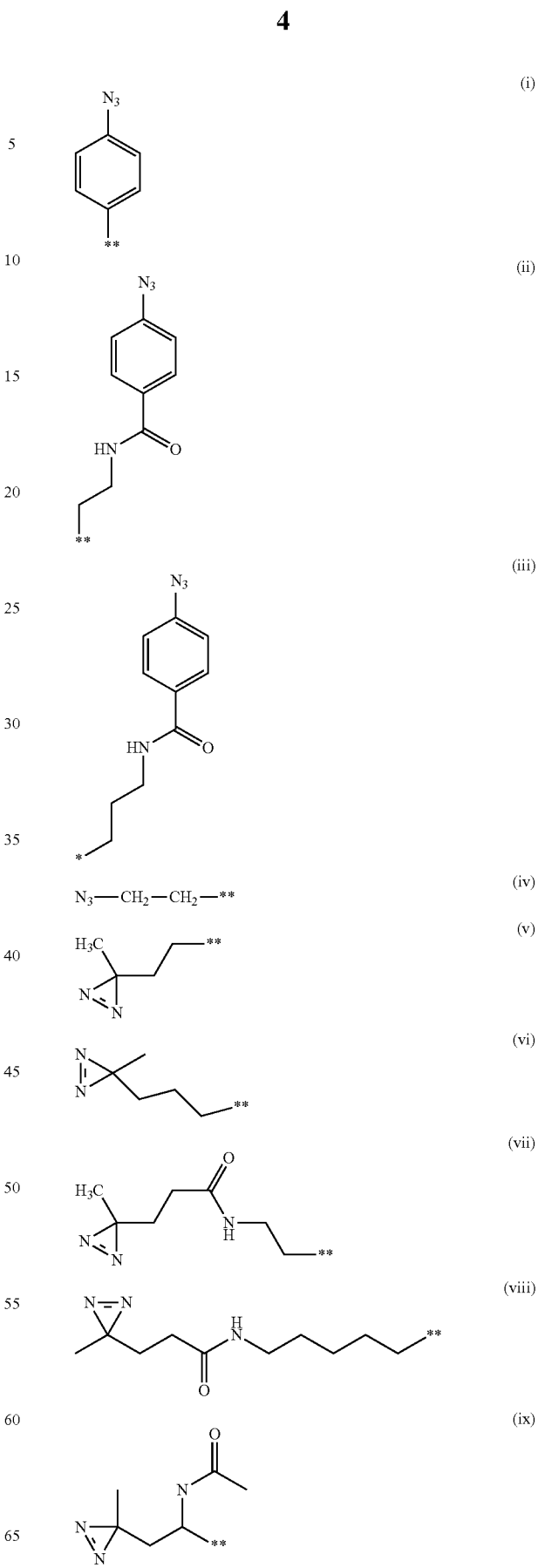

-continued

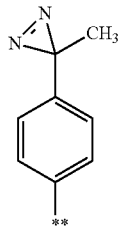
(x)

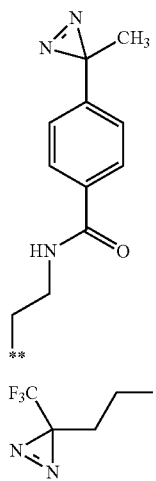
(xi)

(xii)

** represents the bond with the ester group bonded to the polymer PS
(PS—O—CO— group)

Groups (i) and (v) are preferred.

The grafted polysaccharides used according to the invention may especially be prepared by activation of a carboxylic acid X-L-COOH (A) with a carbodiimide (B) (for example 1-ethyl-3-(3-dimethylaminopropyl)carbodiimide hydrochloride)—to form the activated acid (C)—followed by grafting onto the hydroxyl groups of the polysaccharide (synthetic scheme I). The reaction may also be performed in the presence of a second carboxylic acid activator such as N-hydroxybenzotriazoles and N-hydroxysuccinimides, in particular N-hydroxysuccinimide (D) (synthetic scheme II) to form an intermediate (E) before grafting onto the hydroxyl groups of the polysaccharide. The second activator makes it possible to stabilize the activated carboxylic acid, to limit the hydrolysis of the activated carboxylic acid and also to increase the degree of grafting on the polysaccharide.

The reaction may take place in an aprotic or protic solvent. Preferably, the reaction takes place in water at a pH of between 4 and 9 and preferentially between 5 and 7. The reaction is preferably performed at a temperature of between 5° C. and 80° C. and preferentially at room temperature (25° C.).

Synthetic scheme I

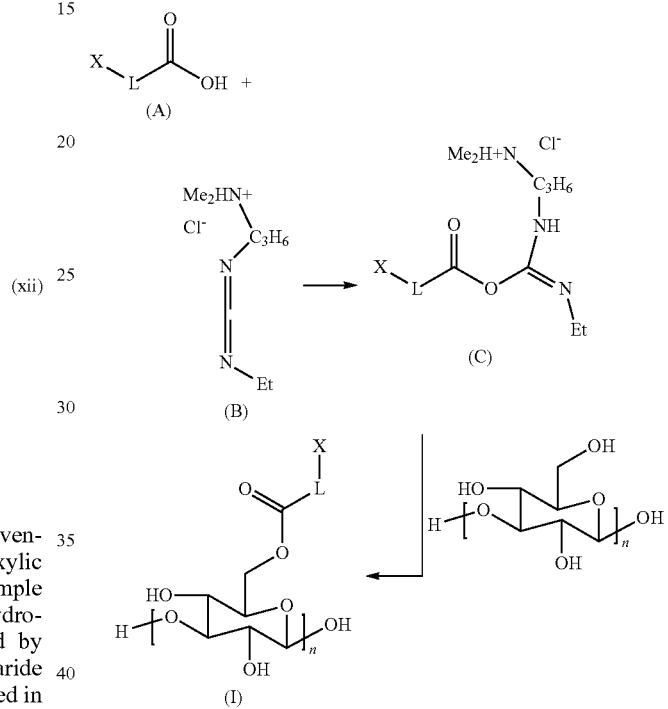

Use of N-hydroxysuccinimide in the synthetic process leads to the reaction scheme described below:

Synthetic scheme II

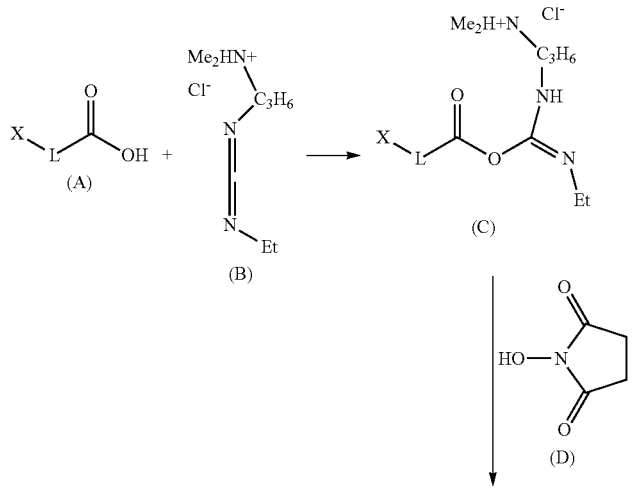

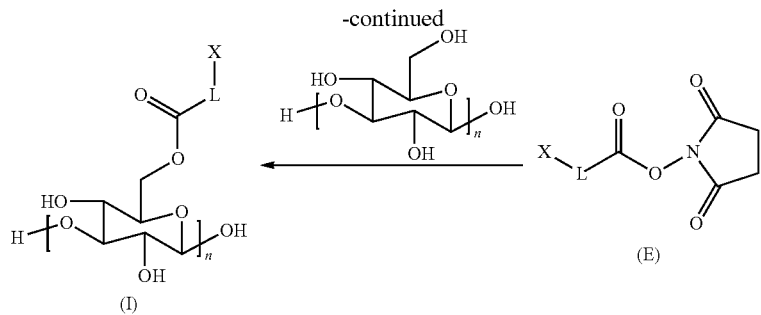

In a simplified manner, the reaction scheme is as follows:

PS—OH+A-O—CO-L-X→PS(OCO-L-X)$_a$(OH)$_b$(C)  (I)

A representing a carboxylic acid-activating group, for instance carbodiimides. Certain compounds X-L-COO-A are available, such as the compounds described below:

| | |
|---|---|
| N-hydroxysuccinimide ester of 4-[3-(trifluoromethyl)diazirin-3-yl] benzoic acid from the company Toronto Research Chemicals | 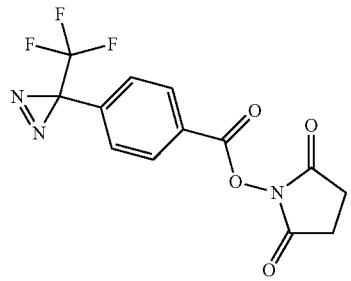 [SMILES: O=C(ON1C(=O)CCC1=O)c1ccc(C2(C(F)(F)F)N=N2)cc1] |
| Succinimidyl-diazirine (SDA from the company ThermoScientific) | 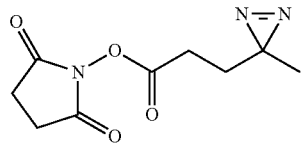 [SMILES: CC1(CCC(=O)ON2C(=O)CCC2=O)N=N1] |
| Sulfo-succinimidyl-diazirine (Sulfo-SDA from the company ThermoScientific) | 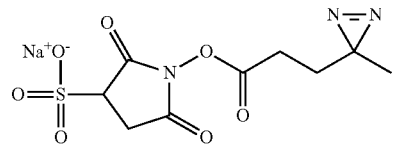 |
| Succinimidyl 6-[4,4-azipentanamido]hexanoate (LC-SDA from the company ThermoScientific) | 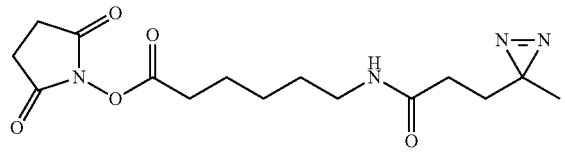 [SMILES: CC1(CCC(=O)NCCCCCC(=O)ON2C(=O)CCC2=O)N=N1] |
| Sulfosuccinimidyl 6-[4,4-azipentanamido] hexanoate (Sulfo-LC-SDA from the company ThermoScientific) | 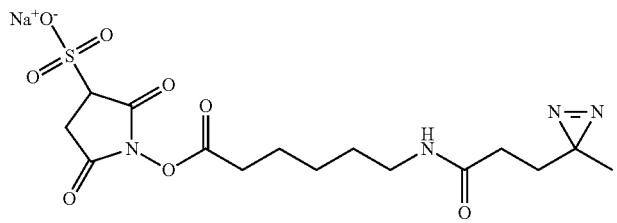 |

Some of the starting non-activated carboxylic acids (X-L-COOH) are commercially available, such as those mentioned in the table below:

| | |
|---|---|
| 4[3-(trifluoromethyl)-3H-diazirin-3-yl]benzoic acid from the company TCI | 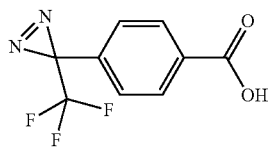 [SMILES: O=C(O)c1ccc(C2(C(F)(F)F)N=N2)cc1] |
| α-(acetylamino)-3-methyl-3H-diazirine-3-propanoic acid from the company ChemStep | 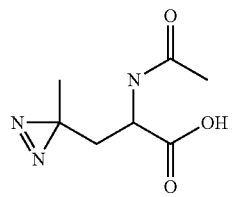 |
| 4-(3-methyl-3H-diazirin-3-yl)butanoic acid from the company FineChemie & Pharma | 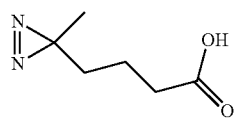 |
| 4-[3-(trifluoromethyl)-3H-diazirin-3-yl]benzenepropanoic acid from the company Dalton Pharma | 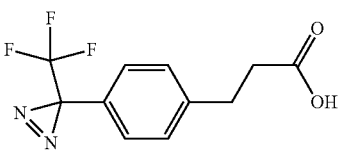 [SMILES: O=C(O)CCc1ccc(C2(C(F)(F)F)N=N2)cc1] |

Advantageously, the grafted polysaccharide polymer has a degree of grafting with photoactive groups ranging from 2% to 50%, preferably ranging from 2% to 40%, preferably ranging from 2% to 30%, preferentially ranging from 4% to 20%, and better still ranging from 4% to 15%. The degree of grafting corresponds to the percentage of OH groups of the polysaccharide that are grafted with a photoactive group —CO-L-X.

By way of example, a degree of grafting of 50% corresponds to half of the OH groups of the polysaccharide grafted with a photoactive group —CO-L-X.

Hyaluronic acid polymers bearing an ester group derived from 4-azidobutyric acid used for forming injectable hydrogels are described in the article "In situ cross-linkable hydrogel of hyaluronan produced via copper-free click chemistry", Akira Takahashi et al., Biomacromolecules, 2013, 14, pages 3581-3588.

Dextran polymers bearing an ester group derived from 4-azidohexanoic acid used as surfactants are described in the article "Polysaccharide-covered nanoparticles with improved shell stability using click-chemistry strategies", Laville M. et al., Carbohydrate Polymers 93 (2013) 537-546.

The grafted polysaccharides of formula (I) defined previously are novel compounds, with the exception of the compounds (I) for which:

PS is dextran and -L-X=—(CH$_2$)$_5$—N$_3$
PS is hyaluronic acid and -L-X=—(CH$_2$)$_3$—N$_3$ One subject of the invention is thus these novel compounds of formula (I).

A subject of the invention is also a composition comprising, in a physiologically acceptable medium, a grafted polysaccharide (I) as defined previously.

The composition used according to the invention is generally suitable for topical application to the skin and thus generally comprises a physiologically acceptable medium, i.e. a medium that is compatible with the skin and/or its integuments. It is preferably a cosmetically acceptable medium, i.e. a medium which has a pleasant color, odor and feel and which does not cause any unacceptable discomfort (stinging, tautness or redness) liable to discourage the consumer from using this composition.

The grafted polysaccharide (I) may be present in the composition according to the invention in a content ranging from 0.1% to 10% by weight, relative to the total weight of the composition, preferably ranging from 0.5% to 10% by weight, preferentially ranging from 1% to 8% by weight and more preferentially ranging from 1% to 6% by weight.

The composition according to the invention may be in any presentation form conventionally used for topical application and especially in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

According to one preferred embodiment of the invention, the composition is in the form of an O/W emulsion or an aqueous gel.

Advantageously, the composition used according to the invention comprises water, in particular in a content which can range from 10% to 99% by weight and preferably ranging from 50% to 99% by weight, relative to the total weight of the composition.

The composition used according to the invention may also contain one or more adjuvants commonly used in the cosmetic field, such as emulsifiers, preserving agents, sequestrants, fragrances, thickeners, oils, waxes or film-forming polymers.

Needless to say, a person skilled in the art will take care to select this or these optional additional compound(s), and/or the amount thereof, such that the antiwrinkle properties of the composition according to the invention are not, or are not substantially, adversely affected by the envisaged addition.

Advantageously, for the process according to the invention, it is possible to apply 0.001 to 0.5 g of cosmetic composition comprising the polysaccharide polymer bearing a grafted uronic acid unit, especially 0.005 to 0.1 g of composition, per $cm^2$ of skin.

The process according to the invention also comprises a step consisting in exposing the skin to light radiation preferably having a wavelength of between 360 and 600 nm.

It is possible to perform this step consisting in applying light radiation before, after or at the same time as (simultaneously with) the step consisting in applying the composition comprising the grafted polysaccharide polymer. Preferably, the two steps take place simultaneously.

Preferentially, in a first stage, the composition comprising the polysaccharide polymer bearing a grafted uronic acid unit is applied to the skin, and then, in a second stage, light radiation is applied to the skin.

It is possible to perform a step of rinsing, for example with water, of the skin between each step of the process.

Preferably, the light radiation used in the process according to the invention has a wavelength of between 400 and 480 nm.

The light radiation preferably has a flux (amount of energy per unit surface area) ranging from 0.1 to 100 $J/cm^2$ and preferably ranging from 1 to 10 $J/cm^2$.

The light radiation may be continuous or non-continuous light.

The light radiation may be natural light (daylight).

The light radiation may be generated by a device, such as arc lamps, such as xenon lamps and mercury lamps; fluorescent lamps; incandescent lamps such as halogens; LEDs and lasers.

Mention may be made especially of goLITE BLU from the company Philips, the lamp Energylight HF 3319/01 from the company Philips, the lamps Dayvia White and Messa from the company Solvital, the lamp Lumino Plus from the company Lanaform, the lamp Medibeam from the company Medibeam, the lamp M-LED 01 from the company Meimed, the lamp Lifemax Light Pod from the company Lifemax, the lamp Lite-Pad from the company Reicorp, and the lamp Camag Box 3 (4×8 W) from the company Camag.

The exposure time of the treated skin to the light radiation provided by a device is preferably at least 5 seconds. Preferably, this exposure time can range from 10 seconds to 15 minutes, in particular between 15 seconds and 10 minutes, even better still between 20 seconds and 5 minutes, regardless of the order of the steps (one before the other or simultaneous).

By way of example, in the case of simultaneous application of the light radiation provided by a device and of the composition comprising the grafted polysaccharide polymer, the light-exposure time may advantageously range from 5 seconds to 15 minutes. It is possible to perform rinsing of the composition.

By way of example, in the case of application of the composition according to the invention followed by exposure to light radiation provided by a device, the light-exposure time may advantageously be between 5 seconds and 15 minutes. It is possible to leave the composition used according to the invention in place for a period of 1 second to 3 hours, before performing the step of applying the light radiation. It is possible to perform rinsing of the composition, after the step of exposure to light radiation.

The exposure time of the treated skin to daylight as light radiation is preferably at least 3 minutes. Preferably, this exposure time may range from 3 minutes to 12 hours, especially between 5 minutes and 90 minutes, better still between 10 minutes and 30 minutes, regardless of the order of the steps (one before the other or simultaneous).

By way of example, in the case of simultaneous application of daylight and of the composition comprising the grafted polysaccharide, the light-exposure time may advantageously range from 3 minutes to 12 hours. It is possible to perform rinsing of the composition.

By way of example, in the case of application of the composition comprising the grafted polysaccharide, followed by exposure to daylight, the light-exposure time may advantageously be between 3 minutes and 12 hours. It is possible to leave the composition according to the invention in place for a period of 1 second to 3 hours, before performing the step of exposure to light radiation.

It is possible to perform rinsing of the composition, after the step of exposure to light radiation, but this is not obligatory.

The step of exposure to light radiation may be repeated several times during the day.

The application of the cosmetic composition used according to the invention is performed according to the usual techniques, for example by application (especially of creams, gels, sera or lotions) to the skin intended to be treated, in particular facial and/or neck skin, especially the skin of the area around the eyes. In the context of this process, the composition may be, for example, a care composition.

The invention will now be described with reference to the following examples, which are given as non-limiting illustrations. The contents are expressed as weight percentages.

SYNTHESIS EXAMPLE 1 (POLYMER 1):
HYALURONIC ACID 6% FUNCTIONALIZED WITH DIAZIRINE GROUPS

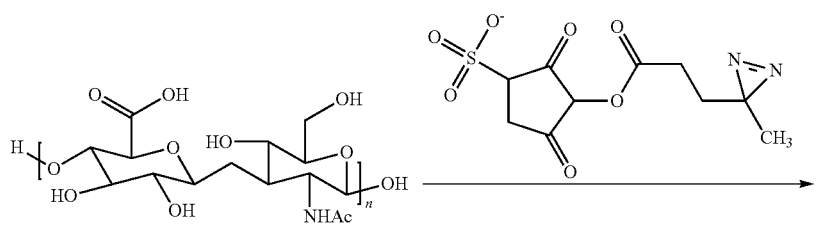

-continued

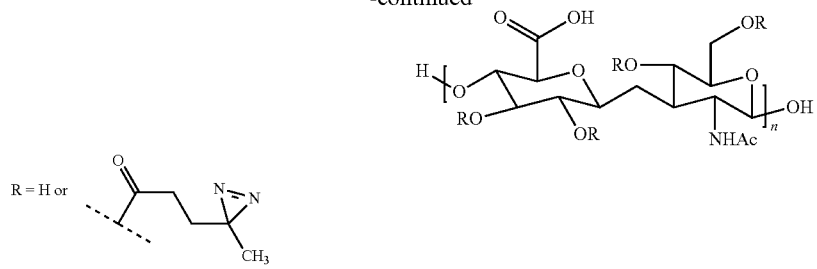

210 mg of hyaluronic acid (Hyacare® 50 from Evonik) were dissolved in 4.2 ml of distilled water in a round-bottomed flask covered with aluminum foil to prevent exposure to light. 50 mg of succinimidyl 4,4'-azipentanoate (sulfo-SDA from the company ThermoScientific) were added, with stirring at a temperature of 5° C. The reaction mixture was stirred for 24 hours while allowing the temperature to rise to 22° C., and maintaining the pH between 6 and 7 by addition of aqueous 0.5 M sodium hydroxide solution and aqueous 0.5 M hydrochloric acid solution.

210 mg of hyaluronic acid (Hyacare® 50 from Evonik) were dissolved in 4.2 ml of distilled water in a round-bottomed flask covered with aluminum foil to prevent exposure to light. 50 mg of succinimidyl 4,4'-azipentanoate (sulfo-SDA from the company ThermoScientific) were added, with stirring at a temperature of 5° C. The reaction mixture was stirred for 24 hours while allowing the temperature to rise to 22° C., and maintaining the pH between 6 and 7 by addition of aqueous 0.5 M sodium hydroxide solution and aqueous 0.5 M hydrochloric acid solution.

The reaction mixture was then introduced into a dialysis tube (Spectra/Por Dialysis Membrane MWCO 3500) and dialyzed in 5 liters of osmosed water for 48 hours, the water being replaced 8 times during this dialysis operation.

The residue deposited in the dialysis tube was extracted with distilled water and lyophilized to obtain a fibrous yellow solid product (250 mg).

The product was stored in an amber-colored flask at −20° C.

The $_1$H NMR analysis in deuterated water: 6% grafting

SYNTHESIS EXAMPLE 2 (POLYMER 2): HYALURONIC ACID 11% FUNCTIONALIZED WITH AZIDE GROUPS 1.63 g (0.01 mol) of 4-azidobenzoic acid were mixed with 100 ml of distilled water in a brown-glass round-bottomed flask. The solution was stirred vigorously and 1.9 g (0.01 mol) of 1-ethyl-3-(3-dimethylaminopropyl)carbodiimide hydrochloride (EDC) were then added, followed by addition of 68 mg (0.5 mmol) of N-hydroxybenzotriazole (HOBt). The pH was adjusted to pH 5.2 by addition of aqueous 0.1 M sodium hydroxide solution. The solution was stirred vigorously for 50 minutes, and a solution of hyaluronic acid (Hyacare® 50 from Evonik) (2 g in 70 ml of distilled water) was then added. The solution was stirred at room temperature (25° C.) for 3 days.

The reaction mixture was then introduced into a dialysis tube (Spectra/Por Dialysis Membrane MWCO 3500) and dialyzed in 5 liters of water for 48 hours, the water being replaced 4 times during this dialysis operation.

The residue deposited in the dialysis tube was extracted with distilled water and lyophilized to obtain a fibrous yellow solid product.

This recovered solid was washed at room temperature in a brown round-bottomed flask using acetone, for 2 hours (100 ml per extraction, 3 extractions being performed).

The solid residue was then filtered off for 5 minutes and then dried under vacuum at room temperature for 12 hours. 1.8 g of a beige-colored solid product (powder) were thus obtained.

The product was stored in an amber-colored flask at −20° C.

The 1H NMR analysis in deuterated water: 11% grafting

SYNTHESIS EXAMPLE 3 (POLYMER 3): ALGINIC ACID 10% FUNCTIONALIZED WITH DIAZIRINE GROUPS

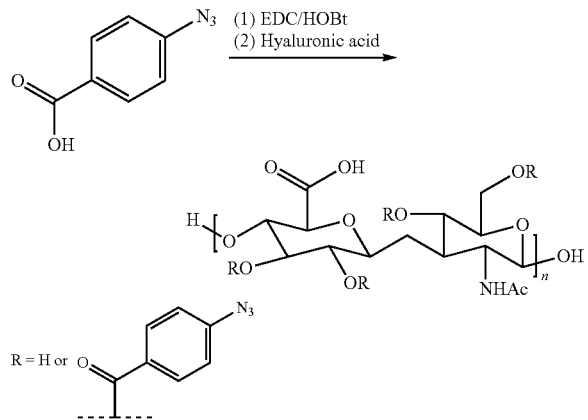

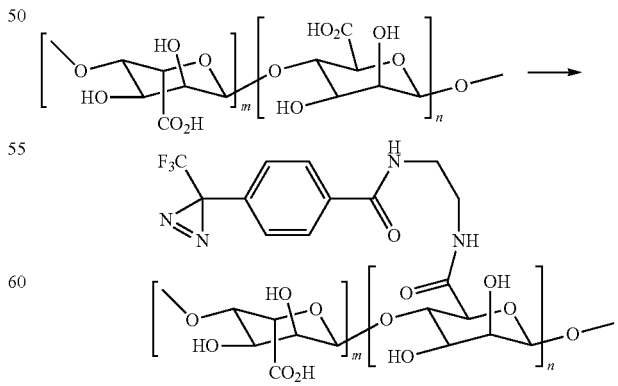

0.65 g (3.68 mol) of alginic acid (Kelcosol from ISP) were mixed with 33 ml of distilled water in a brown-glass round-bottomed flask. The pH was adjusted to pH 3.4-3.6 by addition of aqueous 0.2 M hydrochloric acid solution. The solution was stirred vigorously and 0.71 g (3.68 mmol) of 1-ethyl-3-(3-dimethylaminopropyl)carbodiimide hydrochloride (EDC) in water (3 mL) was then added, followed by 800 mg (3.68 mmol) of N-hydroxysulfosuccinimide. After stirring for 5 minutes, N-(2-aminoethyl)-4-(3-(trifluoromethyl)-3H-diazirin-3-yl)benzamide (1.0 g) was added. The pH was adjusted to pH 4.7 by addition of aqueous 0.2 M hydrochloric acid solution. The solution was stirred at room temperature (25° C.) for 40 hours and then poured into acetone (300 mL). The white precipitate was recovered by filtration. The powder was placed in 40 mL of water and then introduced into a dialysis tube (Spectra/Por Dialysis Membrane MWCO 3500) and dialyzed in 5 liters of water for 3 days, the water being replaced 3 times during this dialysis operation. The product was recovered by lyophilization to give a white powder (600 mg). The product was stored in an amber-colored flask at −20° C.

The 1H NMR analysis in deuterated water: 10% grafting

EXAMPLE 1: DEMONSTRATION OF THE TENSIONING EFFECT OF POLYMERS 1 AND 2

The following compositions were prepared:

Composition 1: aqueous solution containing 5% by weight of AM of hyaluronic acid (Hyacare® 50 from Evonik)

Composition 2: aqueous solution containing 5% by weight of AM of polymer 1

Composition 3: aqueous solution containing 5% by weight of AM of polymer 2

Composition REF: aqueous composition of Hybridur® 875 polymer dispersion from Air Products (aqueous dispersion containing 40% by weight of particles of an interpenetrated network of polyurethane and acrylic polymers) at 7% AM.

The tensioning power of polymers 1 and 2 was compared, in vitro with a reference tensioning polymer: Hybridur® 875 polymer dispersion from Air Products (aqueous dispersion containing 40% by weight of particles of an interpenetrated network of polyurethane and acrylic polymers) and also with reference to hyaluronic acid (Hyacare® 50 from Evonik).

The tensioning effect is measured by an in vitro retraction test. This test consists in quantifying in vitro the tensioning power of a material deposited on an elastomeric substrate (Kimtech nitrile reference 90627 from Kimberley Clark) having a modulus of about 20 MPa and a thickness of 100 μm.

26 μl of each polymer composition were deposited on a rectangular specimen (9×40 mm) of elastomer. Some of the treated specimens were irradiated for 1 minute with an Oriel sun simulator machine from the company Oriel-Lot.

After 3 hours of drying at 22±3° C. and 40±10% relative humidity, the tensioning effect exerted by the polymer deposited on the specimen is directly linked to the decrease in width at the center of the specimen. The tensioning effect (TE1) may then be quantified in the following manner:

tensioning effect (TE1) in $\% = (L_0 - L_1/L_0) \times 100$ $L_0$ = initial width 9 mm and $L_1$ = width after 3 hours of drying The persistence with respect to synthetic sweat of the observed tensioning effect was then evaluated.

The deposits were rinsed by spraying onto the strip, at a distance of 5 cm, 10 μl of aqueous 0.9 M NaCl solution (synthetic sweat).

The deposits were dried for 3 hours at 22±3° C. and 40±10% relative humidity, and the tensioning effect after washing (TE2) was measured again by measuring the width $L_2$ of the specimen.

Tensioning effect (TE2) in $\% = (L_0 - L_2/L_0) \times 100$ with $L_2$ = width of the specimen after rinsing and 3 hours of drying.

The following results were obtained:

| Example | Composition | Polymer | Irradiated (yes/no) | Tensioning effect (TE1) (before washing) | Tensioning effect (TE2) (after washing) |
|---|---|---|---|---|---|
| A | 1 | Hyaluronic acid | No | 33% | 11% |
| B | 2 | Polymer 1 | No | 66% | 33% |
| C | 2 | Polymer 1 | Yes | 66% | 66% |
| D | 3 | Polymer 2 | No | 55% | 22% |
| E | 3 | Polymer 2 | Yes | 55% | 55% |
| F | REF | Hybridur ® 875 polymer dispersion | No | 55% | 22% |

The results obtained show that the polymer of Example 1 and that of Example 2 according to the invention, after irradiation of the deposit (Examples C and E), make it possible to obtain a good tensioning effect before and after washing. The tensioning effect obtained thus shows good persistence with respect to sweat.

EXAMPLE 4

An antiwrinkle gel having the following composition is prepared:

| | |
|---|---|
| polymer of synthesis example 1 | 2 g |
| hydroxyethylcellulose (Natrosol ® 250 HHR CS from Ashland) | 0.3 g |
| Preserving agents qs | |
| Water qs | 100 g |

The composition obtained is applied to the face and the surface of the treated skin is then irradiated with white light (Lite-Pad lamp from the company Reicorp) for 5 minutes. The treatment applied makes it possible to effectively smooth out the wrinkles.

EXAMPLE 5

An antiwrinkle gel having the following composition is prepared:

| | |
|---|---|
| polymer of example 2 | 1 g |
| hydroxyethylcellulose (Natrosol ® 250 HHR CS from Ashland) | 0.3 g |
| Preserving agents qs | |
| Water qs | 100 g |

The composition obtained is applied to the face and the surface of the treated skin is then irradiated with white light (Lite-Pad lamp from the company Reicorp) for 15 minutes. The treatment applied makes it possible to effectively smooth out the wrinkles.

EXAMPLE 6: DEMONSTRATION OF THE TENSIONING EFFECT OF POLYMER 3

The tensioning power of polymer 3 was evaluated according to the protocol described in example 1.
Composition 4: aqueous solution containing 2% by weight of AM of polymer 3
The following results were obtained:

| Example | Composition | Polymer | Irradiated (yes/no) | Tensioning effect (TE1) (before washing) | Tensioning effect (TE2) (after washing) |
|---------|-------------|---------|---------------------|------------------------------------------|-----------------------------------------|
| G | 4 | Polymer 3 | No | 55% | 22% |
| H | 4 | Polymer 3 | Yes | 55% | 55% |
| F | REF | Hybridur ® 875 polymer dispersion | No | 55% | 22% |

The results obtained show that the polymer of example 3, after irradiation of the deposit (example H), makes it possible to obtain a good tensioning effect before and after washing. The tensioning effect obtained thus shows good persistence with respect to sweat.

EXAMPLE 7

An antiwrinkle gel having the following composition is prepared:

| | |
|---|---|
| polymer of example 3 | 1 g |
| hydroxyethylcellulose (Natrosol ® 250 HHR CS from Ashland) | 0.3 g |
| Preserving agents qs | |
| Water qs | 100 g |

The composition obtained is applied to the face and the surface of the treated skin is then irradiated with white light (Lite-Pad lamp from the company Reicorp) for 15 minutes. The treatment applied makes it possible to effectively smooth out the wrinkles.

The invention claimed is:

1. A polysaccharide polymer grafted with photoactive groups of an azide or diazirine of formula (I):

$$PS—(O—CO-L-X)_a(OH)_b \quad (I)$$

in which PS denotes the basic backbone of the polysaccharide bearing the hydroxyl groups;
L is a linear, branched or cyclic, saturated or unsaturated divalent hydrocarbon-based group comprising from 1 to 20 carbon atoms, which may be interrupted with one or more non-adjacent heteroatoms chosen from sulfur, oxygen, or —NH—, —COO—, —CONH—, —O—CO—NH— or —NH—CO—NH— groups, said divalent group optionally substituted with one or more groups chosen from hydroxyl, amine, thiol, carboxylic acid, amide, cyano, and acyl ($C_1$-$C_4$)amino groups;
X denotes the azide or diazirine photoactive group;
a denotes the content of OH groups substituted with the photoactive group;
b denotes the content of unsubstituted free OH groups;
a being between 0.02 and 0.5; b being between 0.5 and 0.98;
and a+b=1;

with the exception of compounds (I) for which:
PS is dextran and -L-X=—$(CH_2)_5$—$N_3$
PS is hyaluronic acid and -L-X=—$(CH_2)_3$—$N_3$.

2. The polymer as claimed in claim 1, wherein the polysaccharide comprises one or more base units chosen from uronic acid, glucuronic acid and mannuronic acid.

3. The polymer as claimed in claim 1, wherein the polysaccharide is chosen from hyaluronic acid, chondroitin, chondroitin sulfate, alginic acid, heparin, heparin sulfate, xanthan gum, dextran and cellulose.

4. The polymer as claimed in claim 1, wherein the polysaccharide is hyaluronic acid or alginic acid.

5. The polymer as claimed in claim 1, wherein a is between 0.02 and 0.4 and b is between 0.6 and 0.98.

6. The polymer as claimed in claim 1, wherein L is chosen from the following groups:

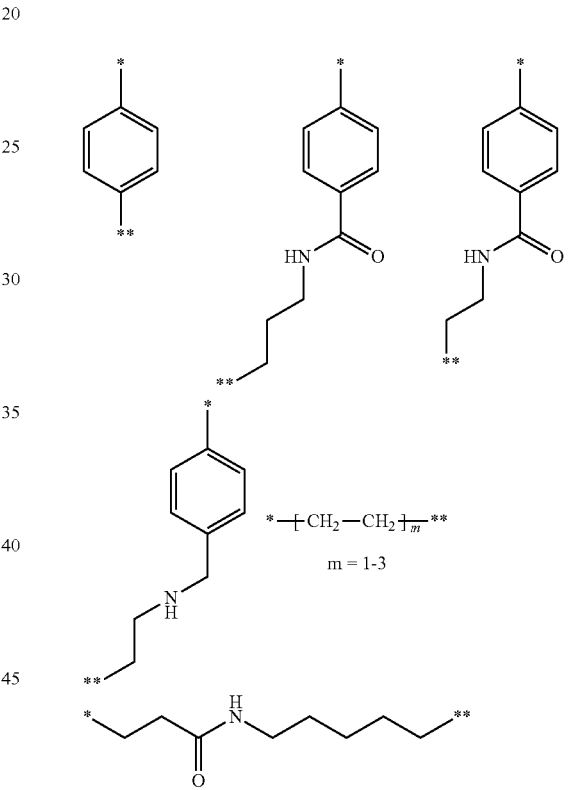

wherein * represents the bond with the photoactive group X
wherein ** represents the bond with the ester group bonded to the polymer PS
(PS—O—CO— group).

7. The polymer as claimed in claim 1, wherein the photoactive group X is chosen from the following groups:

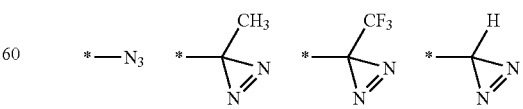

wherein * represents the bond with the photoactive group X.

8. The polymer as claimed in that claim 1, wherein the group X-L- is chosen from:

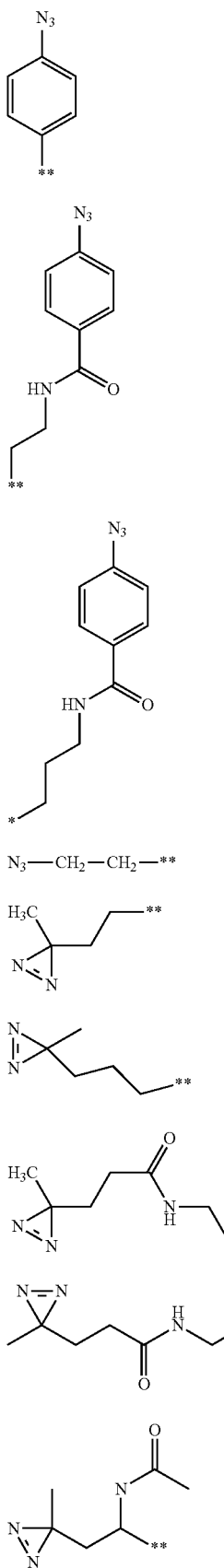
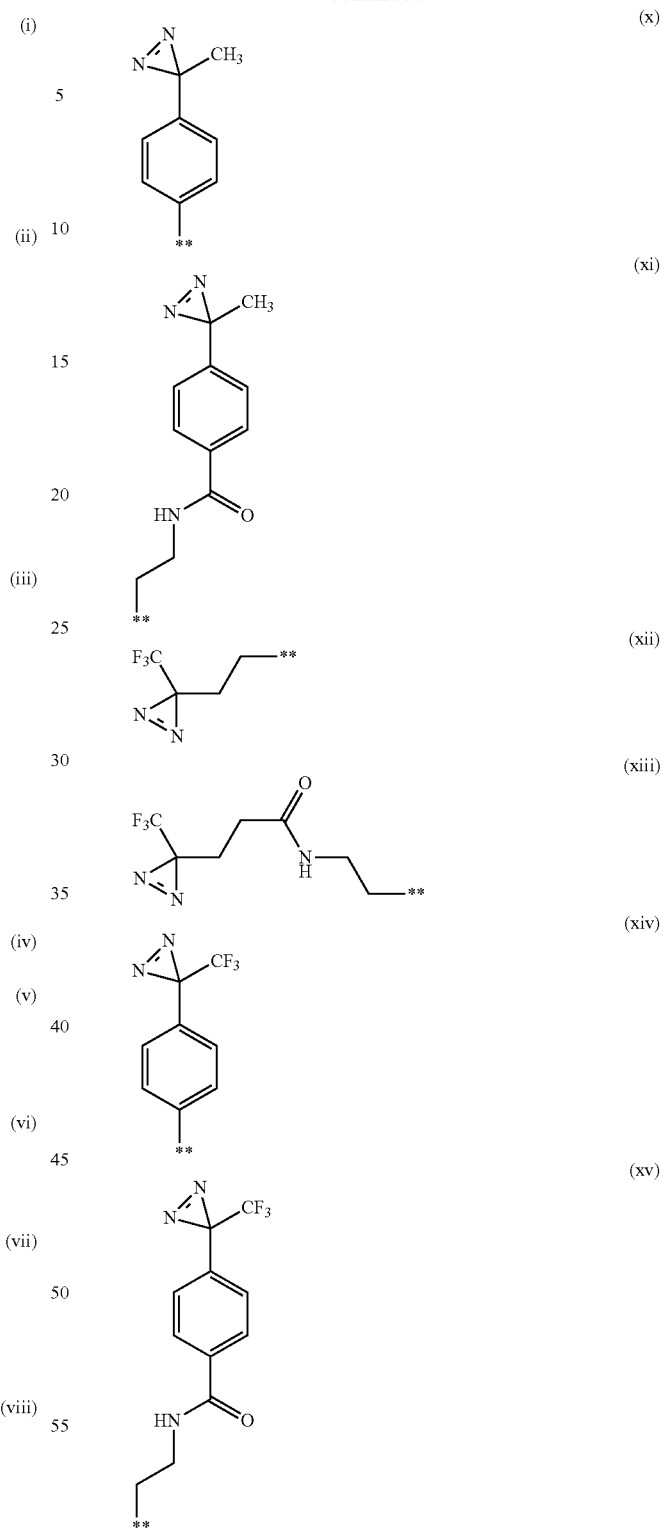
wherein * represents the bond with the photoactive group X
wherein ** represents the bond with the ester group bonded to the polymer PS
(PS—O—CO— group).
9. The polymer as claimed in claim 1, wherein the polymer has a weight-average molecular weight ranging from 5000 daltons to 1,000,000 daltons as determined by liquid chromatography with 0.1 M sodium chloride and 330 mg/l of sodium azide in water as an eluent and dextran as the standard, using Wyatt Optilab T-Rex refractometer and Wyatt Dawn-Heleos II light scattering detectors.

10. A composition comprising, in a physiologically acceptable medium, a grafted polysaccharide (I) as claimed in claim 1.

11. The composition as claimed in claim 10 the grafted polysaccharide (I) is present in a content ranging from 0.1% to 10% by weight, relative to the total weight of the composition.

12. The composition as claimed in claim 10, which comprises a cosmetic adjuvant chosen from water, emulsifiers, preserving agents, sequestrants, fragrances, thickeners, oils, waxes and film-forming polymers.

13. The composition as claimed in claim 10, which is in the form of an oil-in-water emulsion or an aqueous gel.

14. A cosmetic process for caring for the skin comprising:
(i) applying to the skin a composition comprising, in a physiologically acceptable medium, a grafted polysaccharide (I),
(ii) exposing the treated skin to light radiation,
the grafted polymer (I) being a polysaccharide polymer grafted with photoactive groups of an azide or diazirine of formula:

PS—(O—CO-L-X)$_a$(OH)$_b$    (I)

in which PS denotes the basic backbone of the polysaccharide bearing the hydroxyl groups;
L is a linear, branched or cyclic, saturated or unsaturated divalent hydrocarbon-based group comprising from 1 to 20 carbon atoms, which may be interrupted with one or more non-adjacent heteroatoms chosen from sulfur, oxygen, or —NH—, —COO—, —CONH—, —O—CO—NH— or —NH—CO—NH— groups, said divalent group being optionally substituted with one or more groups chosen from hydroxyl, amine, thiol, carboxylic acid, amide, cyano, and acyl (C$_1$-C$_4$)amino groups;
X denotes the azide or diazirine photoactive group;
a denotes the content of OH groups substituted with the photoactive group;
b denotes the content of unsubstituted free OH groups;
a being between 0.02 and 0.5; b being between 0.5 and 0.98;
and a+b=1.

15. The process as claimed in claim 14, wherein the polysaccharide comprises one or more base units chosen from uronic acid, glucuronic acid and mannuronic acid.

16. The process as claimed in claim 14, wherein the polysaccharide is chosen from hyaluronic acid, chondroitin, chondroitin sulfate, alginic acid, heparin, heparin sulfate, xanthan gum, dextran and cellulose.

17. The process as claim 14, wherein the polysaccharide is hyaluronic acid or alginic acid.

18. The process as claimed in claim 14, wherein a is between 0.02 and 0.4 and b is between 0.6 and 0.98.

19. The process as claimed in claim 14, wherein L is chosen from the following groups:

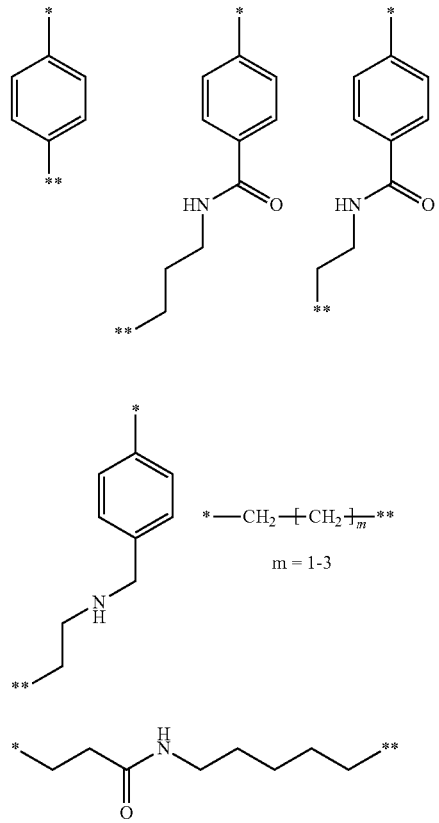

wherein * represents the bond with the photoactive group X
wherein ** represents the bond with the ester group bonded to the polymer PS
(PS—O—CO—    group).

20. The process as claimed in claim 14, wherein the photoactive group X may be chosen from the following groups:

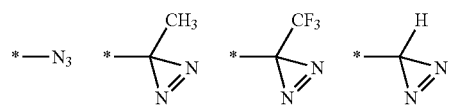

wherein * represents the bond with the photoactive group X.

21. The process as claimed in claim 14, wherein the group X-L- is chosen from:

(i)

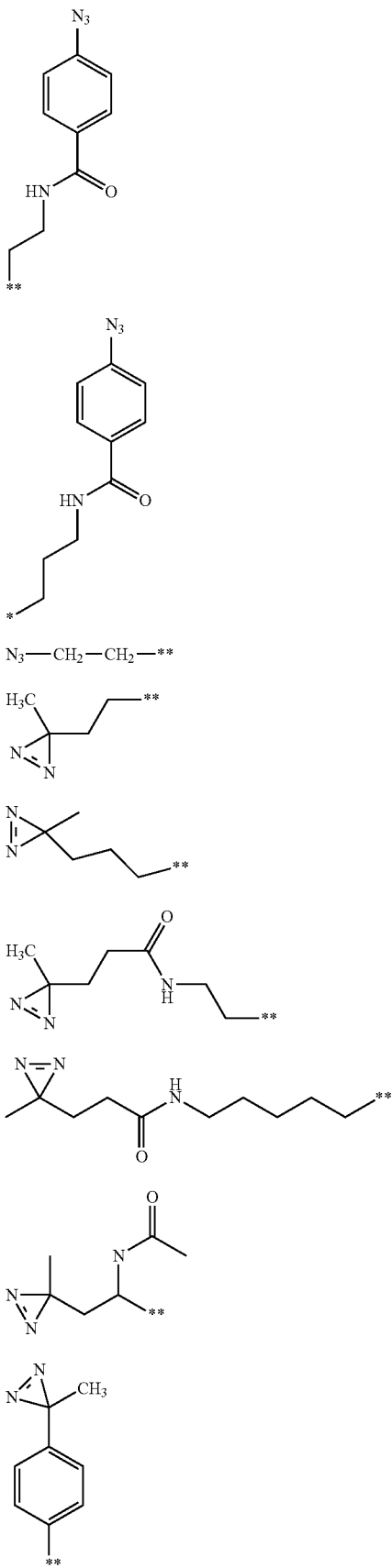
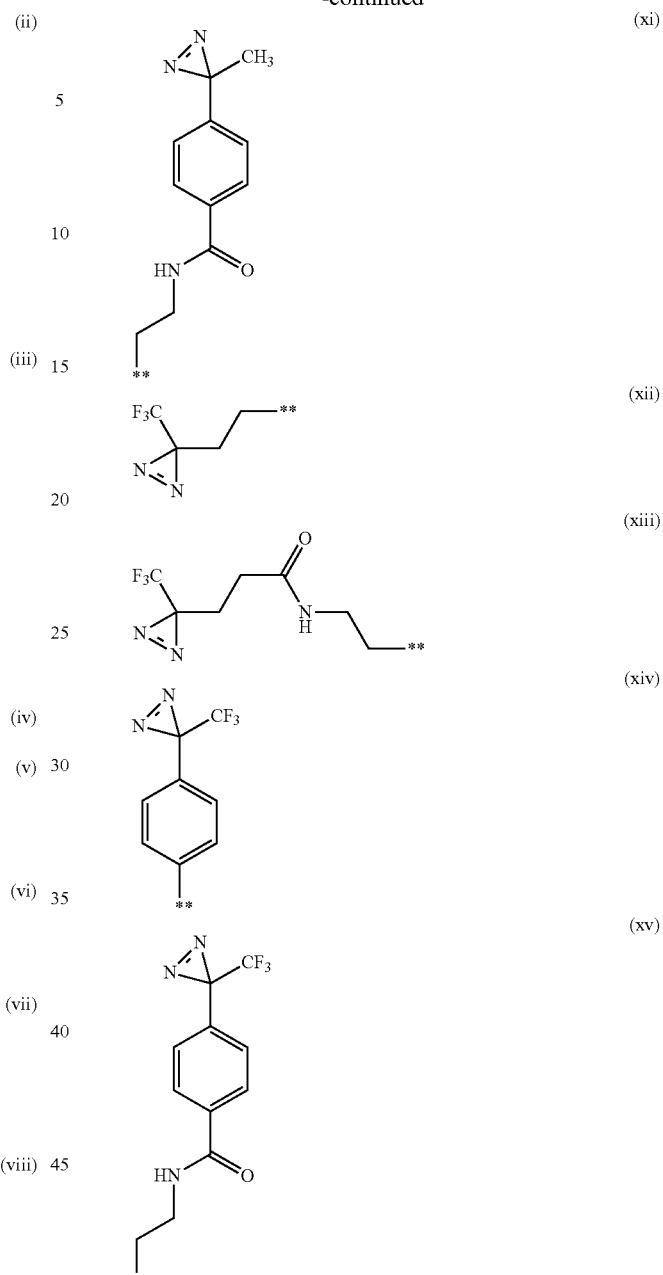

wherein * represents the bond with the photoactive group X
wherein ** represents the bond with the ester group bonded to the polymer PS
(PS—O—CO— group).

22. The process as claimed in claim 14, wherein it the polymer has a weight-average molecular weight ranging from 5000 daltons to 1,000,000 daltons as determined by liquid chromatography with 0.1 M sodium chloride and 330 mg/l of sodium azide in water as an eluent and dextran as the standard, using Wyatt Optilab T-Rex refractometer and Wyatt Dawn-Heleos II light scattering detectors.

23. The process as claimed in claim 14, wherein the grafted polysaccharide (I) is present in a content ranging from 0.1% to 10% by weight, relative to the total weight of the composition.

24. The process as claimed in claim 14, in which the step consisting in applying light radiation is performed after or at the same time as the step consisting in applying the cosmetic composition comprising the grafted polysaccharide (I).

25. The process as claimed in claim 14, in which (ii) applying light radiation is performed after (i) applying the cosmetic composition comprising the grafted polysaccharide (I).

26. The process as claimed in claim 14, wherein the light radiation is natural light or artificial light with a wavelength of between 360 nm and 600 nm.

27. The process as claimed in claim 14, in which the light radiation has a source chosen from arc lamps; fluorescent lamps; incandescent lamps; light emitting diodes and lasers.

28. The process as claimed in claim 14, in which the exposure time to the light radiation is at least 5 seconds.

29. The process as claimed in claim 14, wherein the composition is applied to wrinkled skin.

* * * * *